(12) United States Patent
Miller et al.

(10) Patent No.: US 11,547,292 B2
(45) Date of Patent: Jan. 10, 2023

(54) VAGINAL SPECULUM

(71) Applicant: Cyalume Technologies, Inc, West Springfield, MA (US)

(72) Inventors: James Miller, Fishers, IN (US); Eric Domingos, Chicopee, MA (US); Joseph Longo, Feeding Hills, MA (US)

(73) Assignee: Cyalume Technologies, Inc., West Springfield, MA (US)

( * ) Notice: Subject to any disclaimer, the term of this patent is extended or adjusted under 35 U.S.C. 154(b) by 416 days.

(21) Appl. No.: 16/559,340

(22) Filed: Sep. 3, 2019

(65) Prior Publication Data

US 2020/0069171 A1 Mar. 5, 2020

Related U.S. Application Data

(60) Provisional application No. 62/726,949, filed on Sep. 4, 2018.

(51) Int. Cl.
*A61B 1/32* (2006.01)
*A61B 1/06* (2006.01)

(52) U.S. Cl.
CPC . *A61B 1/32* (2013.01); *A61B 1/06* (2013.01)

(58) Field of Classification Search
CPC .................................... A61B 1/06; A61B 1/32
USPC ......................................................... 600/223
See application file for complete search history.

(56) References Cited

U.S. PATENT DOCUMENTS

| 2,672,859 | A | * | 3/1954 | Jones | A61B 1/32 600/205 |
|---|---|---|---|---|---|
| 3,246,646 | A | | 4/1966 | Murphy, Jr. | |
| 5,052,372 | A | | 10/1991 | Shapiro | |
| 5,179,938 | A | * | 1/1993 | Lonky | A61B 1/31 600/222 |
| 5,329,938 | A | | 7/1994 | Lonky | |
| 5,465,709 | A | * | 11/1995 | Dickie | A61B 1/32 600/223 |
| 6,432,048 | B1 | | 8/2002 | Francois | |
| 7,060,029 | B1 | | 6/2006 | Hajianpour | |
| 9,326,671 | B2 | | 5/2016 | Roeloffs | |
| 9,332,898 | B2 | | 5/2016 | McMahon et al. | |
| 9,532,706 | B2 | | 1/2017 | McMahon et al. | |
| 9,724,124 | B2 | | 8/2017 | Li et al. | |
| 9,913,577 | B2 | | 3/2018 | Swift | |

(Continued)

FOREIGN PATENT DOCUMENTS

| EP | 1006859 B1 | 6/2000 |
|---|---|---|
| GB | 2349826 A | 11/2000 |

(Continued)

OTHER PUBLICATIONS

International Searching Authority; PCT International Search Report and Written Opinioin of the International Searching Authority; published Jan. 13, 2020.

*Primary Examiner* — Jessica Weiss

(74) *Attorney, Agent, or Firm* — Indiano Law Group LLC; E. Victor Indiano; John T. "Woods

(57) ABSTRACT

A speculum includes a first blade member and a second blade member. Each of the first and second blade members extend from a proximal end to a distal end. A speculum control includes a control nut threadingly engaged with a threaded shaft. Internal threads of the control nut are oversized relative external threads of the threaded shaft such that the control nut freely spins upon the threaded shaft.

22 Claims, 18 Drawing Sheets

(56) References Cited

U.S. PATENT DOCUMENTS

| | | | |
|---|---|---|---|
| 2003/0105387 A1* | 6/2003 | Frumovitz | A61B 1/32 600/220 |
| 2003/0176772 A1* | 9/2003 | Yang | A61B 1/0669 600/220 |
| 2004/0133077 A1 | 7/2004 | Obenchain et al. | |
| 2005/0065496 A1* | 3/2005 | Simon | A61M 16/0409 604/500 |
| 2005/0277811 A1 | 12/2005 | Richards et al. | |
| 2009/0203968 A1* | 8/2009 | Winslow | A61B 1/32 600/220 |
| 2009/0312610 A1 | 12/2009 | Buchok et al. | |
| 2014/0039266 A1* | 2/2014 | Porat | A61B 1/012 600/205 |
| 2015/0112148 A1 | 4/2015 | Bouguet | |
| 2017/0181605 A1 | 6/2017 | Lalli et al. | |
| 2017/0181607 A1 | 6/2017 | Lalli et al. | |
| 2018/0249943 A1* | 9/2018 | Moein | A61K 31/4166 |
| 2018/0317746 A1 | 11/2018 | Lalli et al. | |

FOREIGN PATENT DOCUMENTS

| | | | |
|---|---|---|---|
| GB | 2464934 B | 10/2012 | |
| GB | 2500241 B | 4/2018 | |
| WO | WO-9922637 A1 * | 5/1999 | A61B 1/32 |
| WO | 03075979 A2 | 9/2003 | |
| WO | WO-03075979 A2 * | 9/2003 | A61C 1/088 |
| WO | 1006131770 | 12/2006 | |

\* cited by examiner

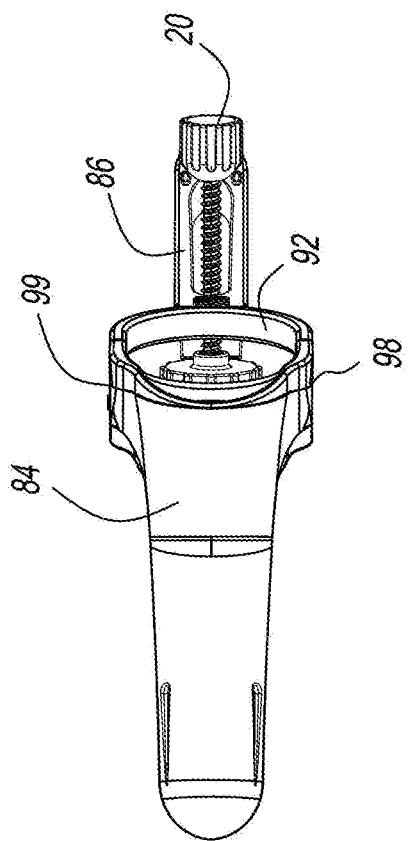
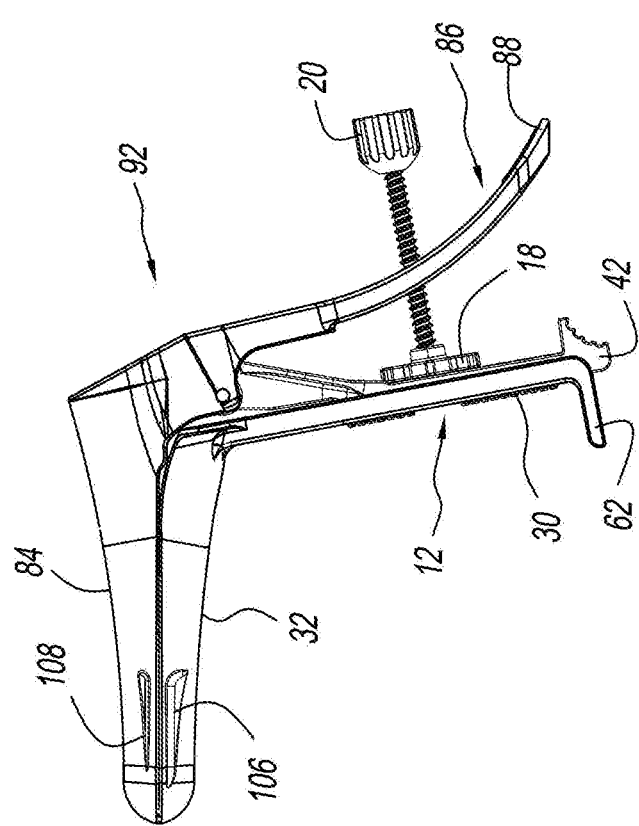
FIG. 5
FIG. 4

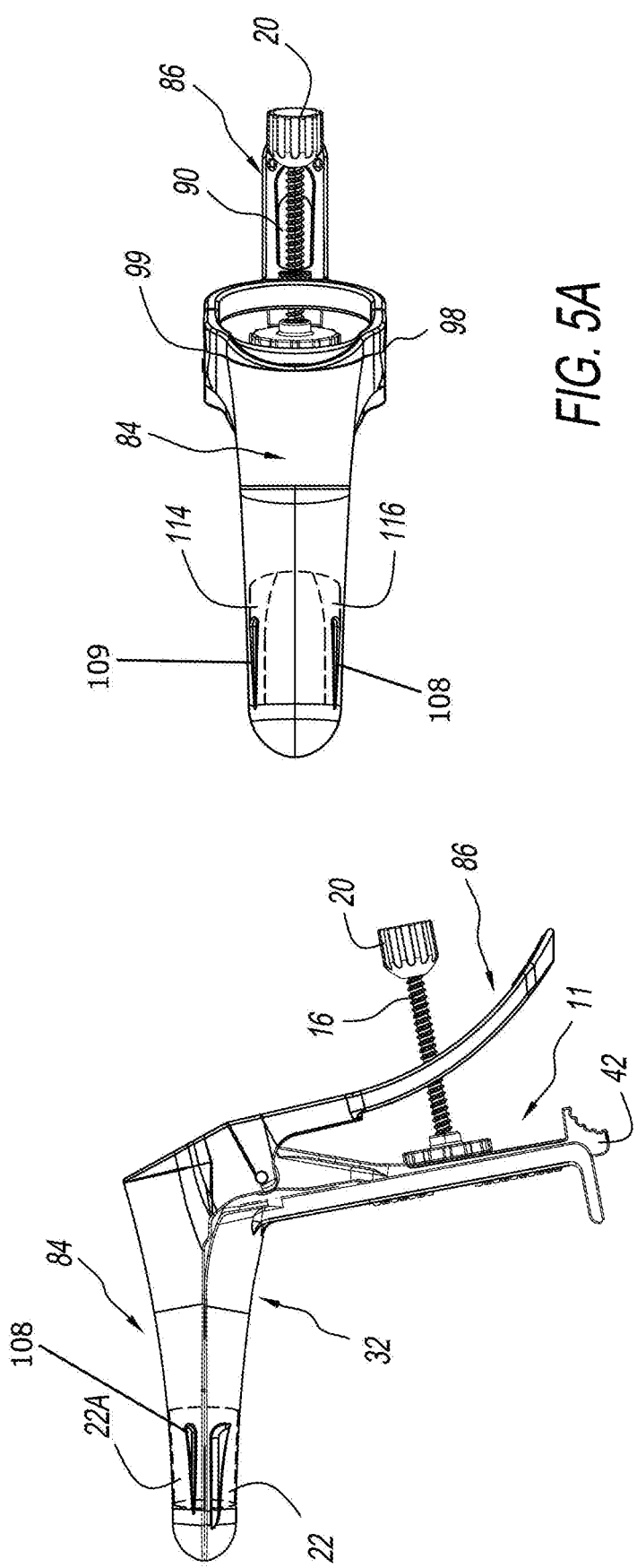

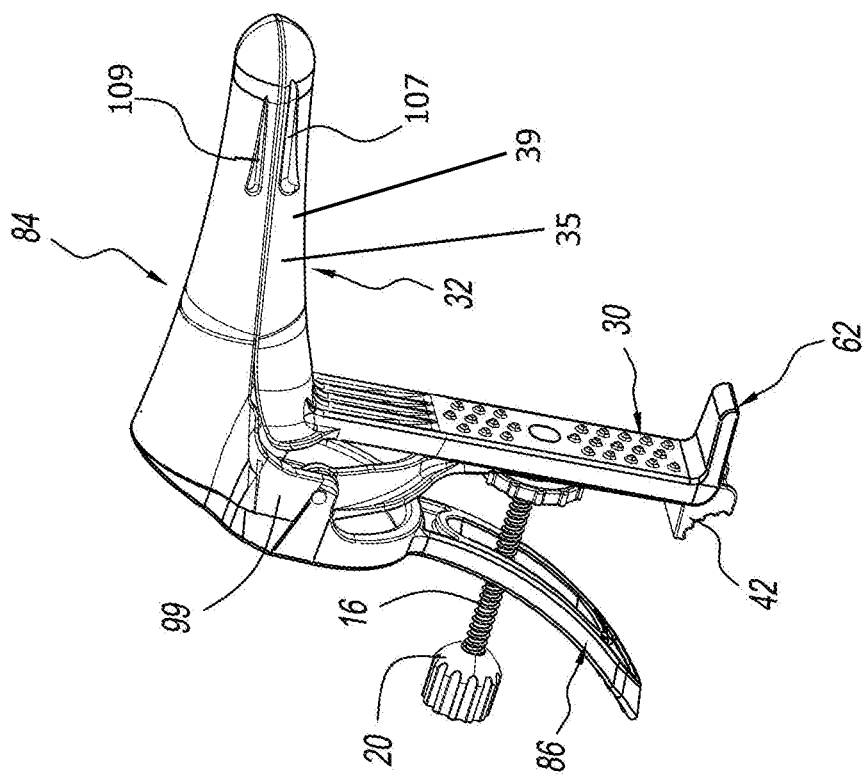
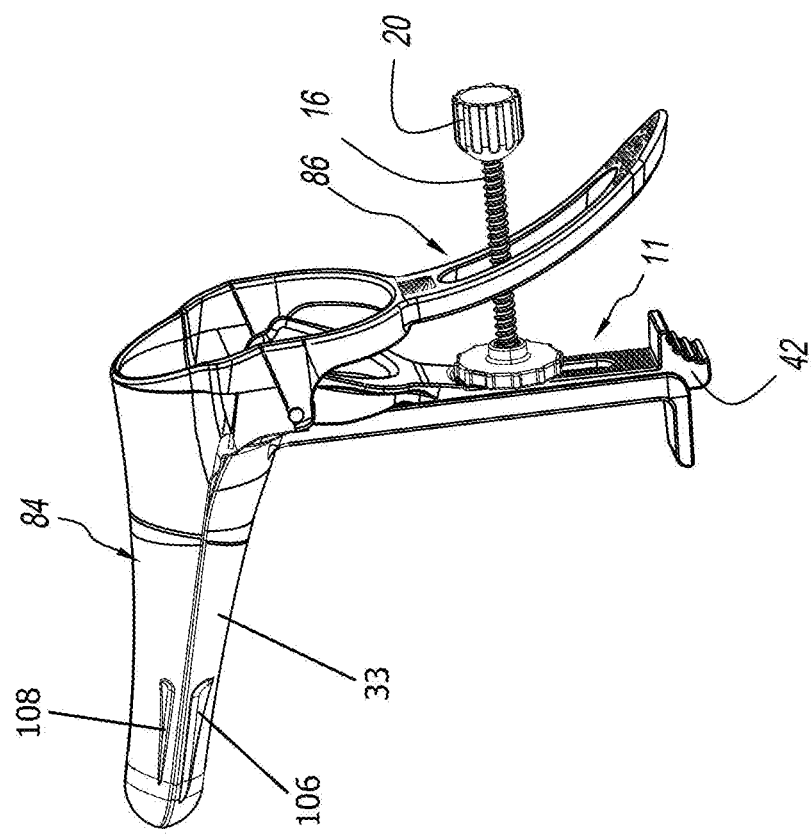
FIG.11
FIG.10

VAGINAL SPECULUM

CROSS REFERENCE TO RELATED APPLICATIONS

The present application claims the benefit of U.S. Provisional Patent Application No. 62/726,949, filed Sep. 4, 2018, the entire contents of which are expressly incorporated herein by reference.

TECHNICAL FIELD OF THE INVENTION

The technical field generally relates to medical instruments, and specifically to vaginal speculums.

BACKGROUND

Medical practitioners, and especially gynecologists, have employed vaginal speculums to aid them in examining the vagina and cervix of mammalian female patients. U.S. Pat. No. 4,766,887 Cecil, Jr. et al. and U.S. Pat. No. 3,716,047 to W. C. Moore et al. disclose typical vaginal speculum designs.

Most vaginal specula include a handle portion, a lower blade, and an upper blade. The lower and upper blades are typically shaped and sized to facilitate insertion into and placement against the walls of the vagina, and to better spread apart the opening of the vagina to facilitate a visual examination of the vaginal and cervical area and/or the insertion of medical instruments therein.

In use, the doctor inserts a distal end of the blades into the vaginal opening and inserts at least a portion of the blades into the vagina. The doctor then spreads the blades apart and looks through an aperture at the proximal end of the speculum, and into the space between the upper and lower blades to examine the vaginal cavity. The aperture of the speculum is the opening at the proximal end between the upper and lower blades.

A lighting mechanism can be employed in combination with the speculum as is shown in the '047 Patent to W. C. Moore. Lighting mechanisms enable light to shine directly into the space between the upper and lower blades, to illuminate, for example, the vaginal canal to assist a gynecologist in performing a pelvic examination. Alternately, light can be transmitted through the acrylic in a tube lighting process, so that the blades themselves can conduct light to thereby better illuminate the interior of the vagina.

Typically, this illumination occurs through electricity, a battery and an incandescent or LED light mechanism. In addition to light being provided by bulb type light, light can be provided by a chemical luminescence type lighting system.

Two examples of medical devices that employ chemical luminescence systems are shown in U.S. Pat. No. 5,465,709 to Robert G. Dickie, 14 Nov. 1995, and PCT Patent Publication No. WO2003-0757982 to James S. Simon and Robert. Although the devices disclosed in the above references have the potential to perform their intended function well, room exists for improvement.

A first area of improvement relates to the lighting system for the speculum. A battery powered light is often employed for lighting the speculums. It is well known that the use of batteries results in environmental and monetary cost issues that adversely impact the production of speculums.

Another area where room for improvement exists is to improve the mechanical operation of the device. In particular, the two-piece adjustment mechanisms employed by most current disposable speculums have a disadvantage of requiring separate elevation and spread-width controls. Also, most devices employ a ratchet mechanism which typically makes an unpleasant ratcheting sound when actuating.

Additionally, most currently employed ratchet mechanisms employ one-way ratchets. These one-way ratchets have caused problems as medical practitioner and doctors have, on occasion, had difficulty disengaging the speculum from the patient because the speculum becomes stuck in an open position because of the ratchet mechanism. At times, ratchet mechanisms have become unworkable or difficult to operate to release the speculum. In some extreme cases, medical practitioners have been required to break the blades of the speculum in order to remove it from its position of insertion in the patient.

SUMMARY

In accordance with the present invention, a disposable gynecological speculum is provided. The speculum includes a yoke member that serves as a frame, and a first speculum member. The speculum member includes a handle portion that is engageable with the yoke member, and a blade portion that is insertable into a vaginal cavity of the patient.

The device further includes a second speculum member that also includes a handle portion and a blade portion. The second speculum member portion is pivotably coupled to the yoke so that the second blade member may pivot with respect to the first blade member, to vary the distance between the first and second blade members to thereby help to spread open the cavity in which the speculum blades are inserted.

The first handle portion includes a track for receiving the yoke so that the yoke is variably slidably positionable relative to the first handle portion. A threaded rod member has a first end that is engageable with the yoke and a second end that extends in a general proximal direction from the yoke. A first or elevation nut is threadedly engageable with the yoke and can be threaded into position where it engages the yoke, to prevent movement between the yoke relative to the first handle portion of the first speculum member. Alternately, the elevation nut may be loosened to permit the relative movement of the yoke and the first handle.

The second speculum member handle portion includes an aperture through which the threaded rod extends. A second or spread control nut is coupled to the threaded rod and can engage the handle portion of the second handle to thereby maintain the desired pivot position and spread angle of the second blade with respect to the first blade.

One feature of the present invention is that a the single threaded rod member having a pair of engageable nuts is provided that enables the user to have, on one member, both elevation control and elevation locking along with spreading control and spreading locking. This feature has the advantage of making the device easier to use and less prone to lock up. A preliminary test conducted by the Applicant using a Ningbo WellMedLab vaginal speculum tester model number KRQ0336B demonstrated that the deflection and strength characteristics of the present invention generally meet or exceed the deflection and strength characteristics of competitive prior art "ratchet mechanism" speculums, thus demonstrating operational compatibility of the Applicant's inventive design.

In a preferred embodiment of the present invention, a chemiluminescence member is provided. The chemical luminescence member comprises a light cartridge. The light cartridge comprises a container having an exterior, and a hollow interior. The hollow interior is provided for containing a chemiluminescent chemical, such as the chemical luminescent system described in Earl Cranor et al., U.S. Pat. No. 9,090,821, and Cranor Patent Application Publication Numbers 2012/097064 and 2014/0353559 and others, all of the disclosures of which are hereby incorporated by reference. The exterior of the light cartridge is sized and positioned to fit within the interior of the blade, and includes a coupler mechanism so that the cartridge can be coupled to the blade. Preferably, the cartridge mechanism and coupling mechanism are configured so that the cartridge mechanism can position the light cartridge adjacent to the distal end of the blades. Additionally, the light cartridge preferably has a proximally facing opaque cap that is most preferably made from a black plastic. The use of the opaque proximal facing surface has the advantage of enhancing the user's vision by reducing the amount of light from the light cartridge that is being shined directly into the user's eyes.

These and other features of the present invention will become apparent to those skilled in the art upon a review of the drawings and detailed description present below, that represent the best mode of practicing the invention perceived presently by the Applicant.

BRIEF DESCRIPTION OF DRAWINGS

FIG. 4 is a side view similar to FIG. 3, except showing the blades in the closed position;

FIG. 4A is a side view similar to FIG. 4 with the blade closed, except showing first and second light cartridges inserted into the speculum with the first light cartridge being affixed to the upper blade, and the second cartridge affixed to the lower blade;

FIG. 5 is a top view of the speculum of the present invention;

FIG. 5A is a top view, similar to FIG. 5 showing a light cartridge engaged with the lower blade;

FIG. 5B is a sectional view taken generally along lines 5B-5B, showing the light cartridge coupled to the bottom blade of the speculum;

FIG. 10 is a proximal end biased perspective view of the speculum showing the blades in the unelevated, and the blade closed position wherein the blades engage each other;

FIG. 11 is a distal end biased perspective view of the speculum in the unelevated and closed position;

DETAILED DESCRIPTION

Figure 1:
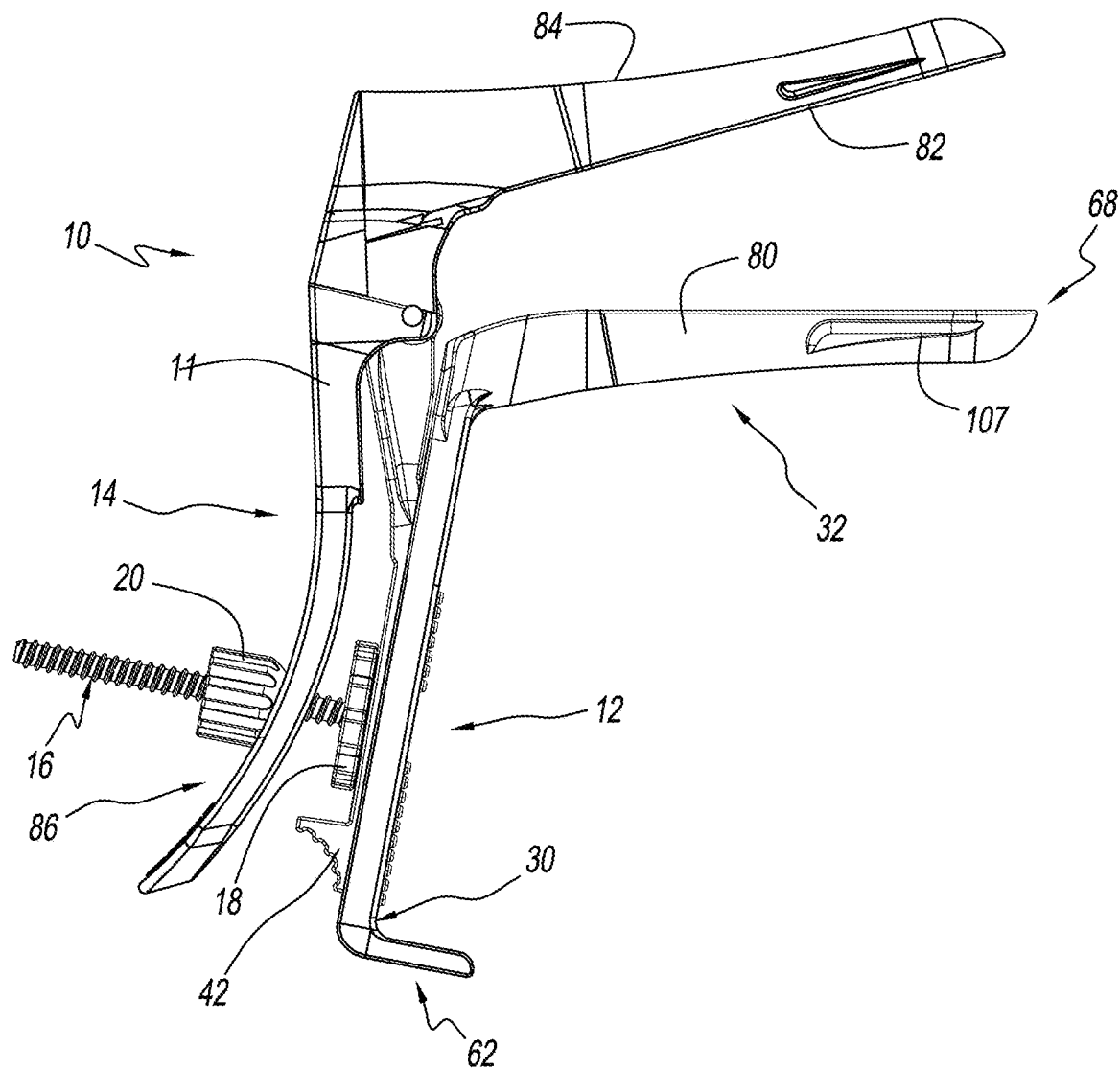
FIG. 1 is a side view of the assembled speculum of the present invention, without the light cartridge inserted therein.
Figure 1A:
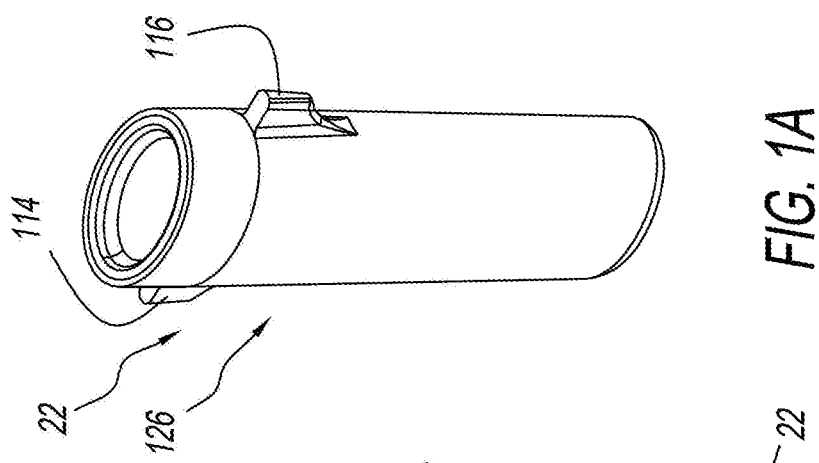
FIG. 1A is a perspective view of the light cartridge of the present invention with the top cap removed.
Figure 1B:
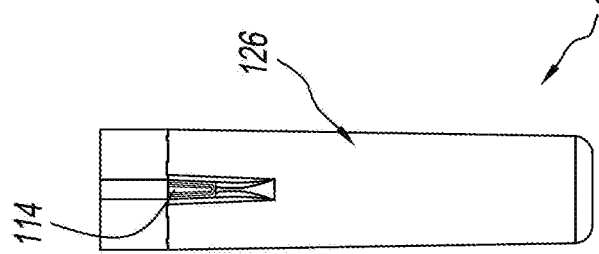
FIG. 1B is a side view of a light cartridge of the present invention.
Figure 1C:
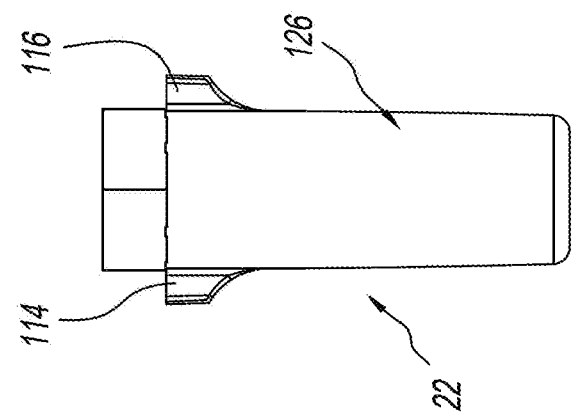
FIG. 1C is a front view of the light cartridge.
Figure 1D:
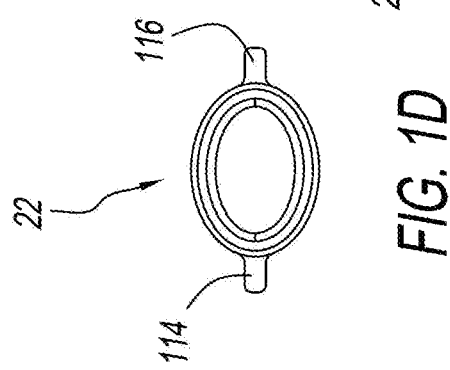
FIG. 1D is a top view of the light cartridge.
Figure 3:
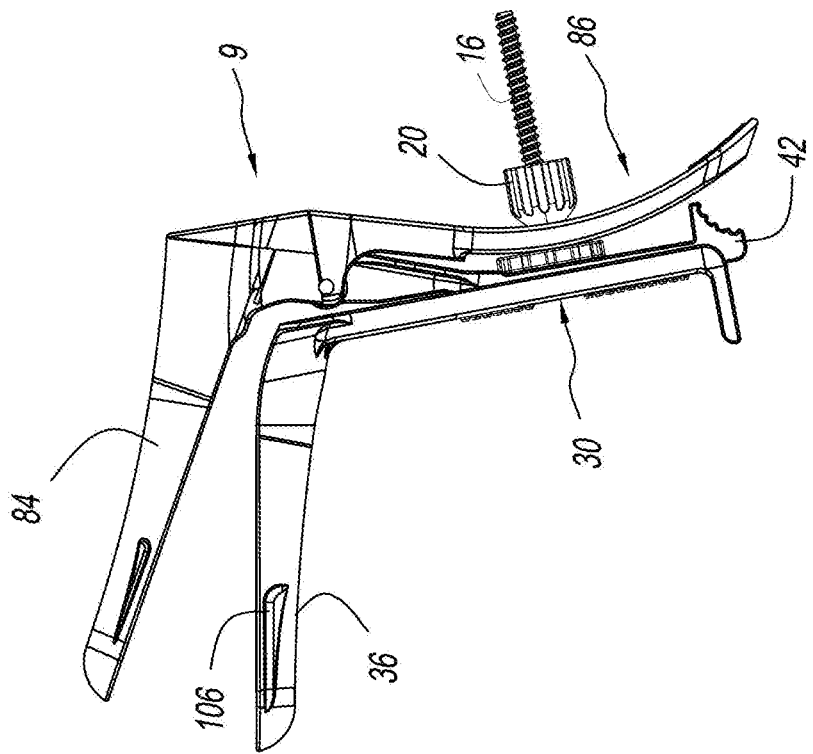
FIG. 3 is a side view showing the blades in their spread position.
Figure 2:
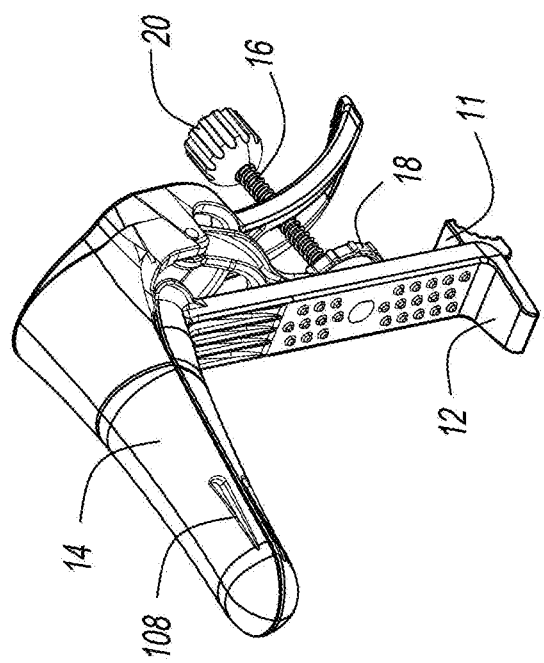
FIG. 2 is a perspective frontal view of the speculum of the present invention with the light cartridge removed.
Figure 3A:
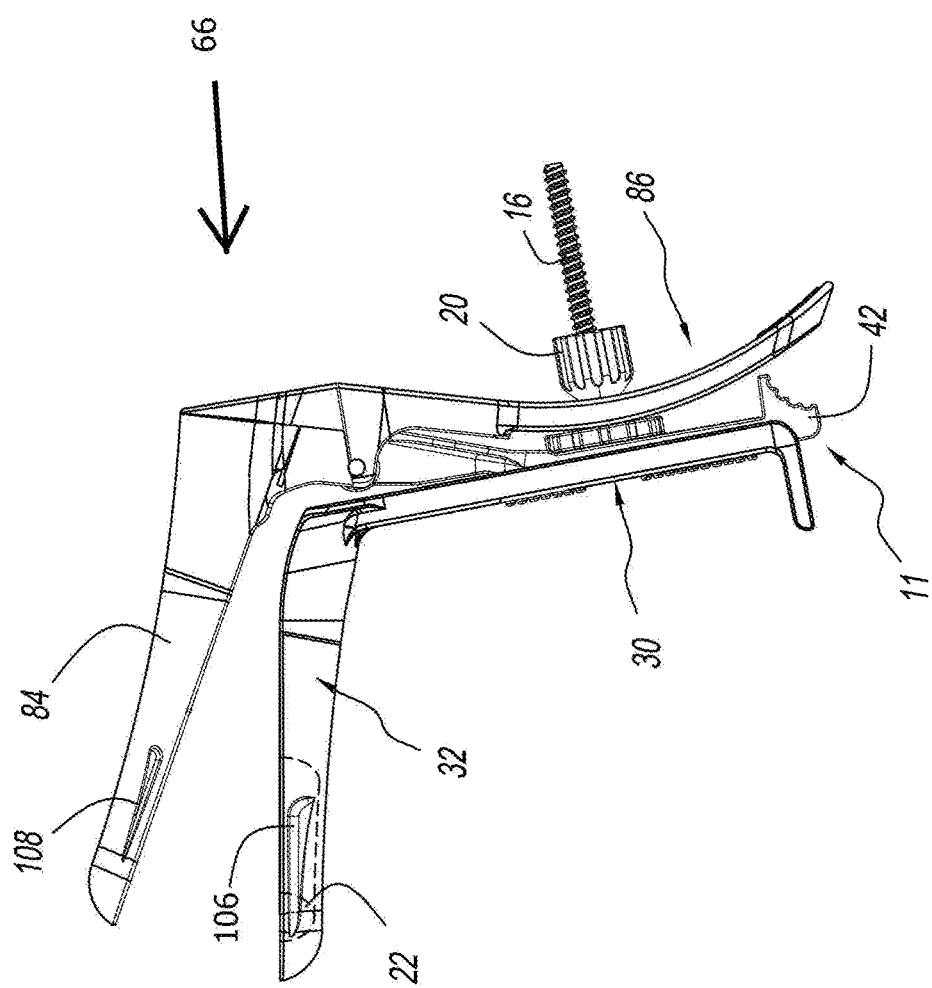
FIG. 3A is a side view with the blades spread apart, similar to FIG. 3, except showing the light cartridge inserted into engagement with the lower blade.
Figure 2A:
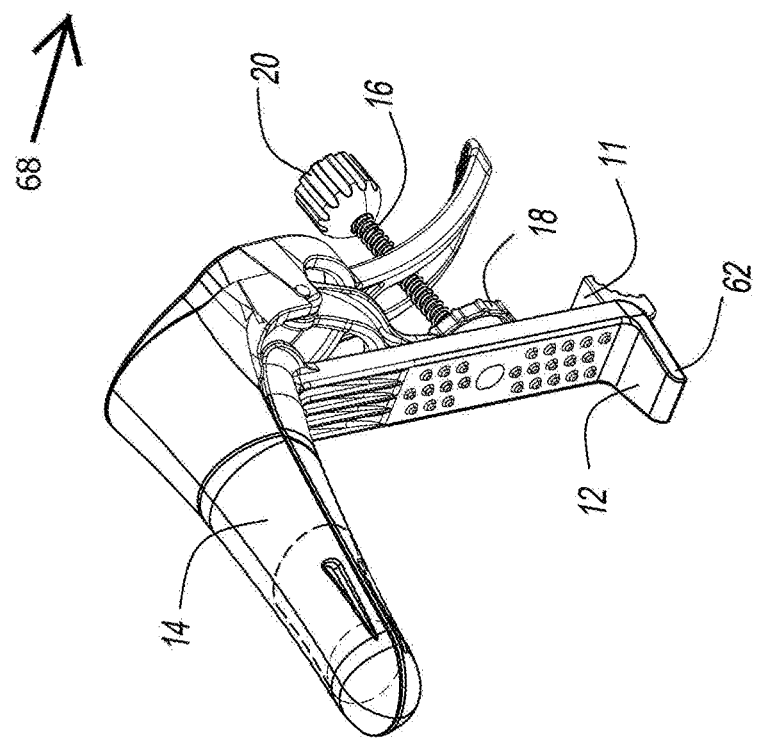
FIG. 2A is a perspective view similar to FIG. 2, except showing the light cartridge coupled to the blade of the present invention.
Figure 7:
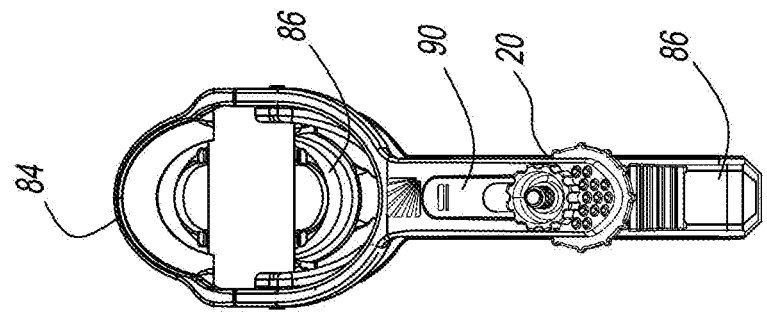
FIG. 7 is a proximal end view of the speculum to illustrate the aperture, formed at the proximal end that enables the doctor to look through the blades, into the end of the cavity into which they were inserted.
Figure 6:
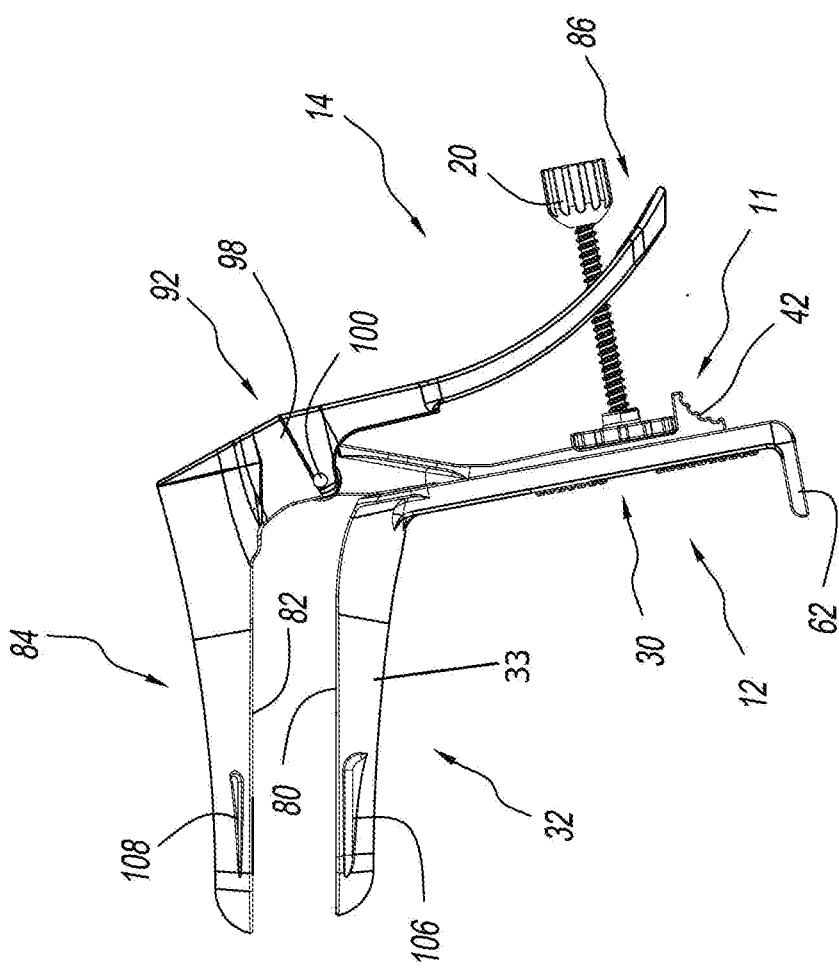
FIG. 6 is a side view of the present invention, showing the blades in an elevated position wherein the blades are disposed generally parallel, but elevated to provide a spacing between the blades.

For purposes of promoting an understanding of the principles of the invention, reference will now be made to the embodiments illustrated in the drawings and specific language will be used to describe the same. It will nevertheless be understood that no limitation of the scope of the invention is thereby intended. Furthermore, any alterations and further modifications in the illustrated device, and any other applications of the principles of the invention as illustrated therein are contemplated as would normally occur to one skilled in the art to which the invention relates.

In the figures, the speculum 10 of the present invention includes a yoke member 11, a first speculum member 12, a second speculum member 14, a threaded rod member 16, a first or elevation control member, here shown as elevation control nut 18, and a second or spread control nut 20. The first control nut member 18 includes a grip-enhancing ridge containing an outer surface 23 and internal female threads 25 in its central aperture 27. The second control nut 20 includes a grip enhancing ridged outer surface 41, and a central aperture 43 containing female threads 45 designed and configured for loosely engaging the male outer threads 116 of threaded rod 16, so that the control nut 20 may spin freely at least through about 720 degrees of rotation, and preferably about 1,440 degrees of rotation when a conventional user's thumb induced rotational force is exerted on the control nut 20. The control nuts and the threaded shaft can be formed of a polymer.

The yoke member 11 is best shown in FIGS. 1, 9-11 and 14. The yoke member 11 includes a slidable base member 24, and an upper, "U" shaped yoke portion 26, to give the yoke an overall "Y" shaped configuration. The lower base member 24 generally has a rectangularly trough shaped configuration (in cross section) that defines a channel between the upright sidewall members 36 of the trough and includes a base wall 32 and first and second upstanding side walls 36 that are sized and configured for being slidably received by corresponding upstanding side walls 40 of the first handle portion 30 of the first speculum member 12.

The yoke member 11 is slidably movable along the first speculum member 12 handle portion 30 in a generally axial direction. At the lower end of the base 24 of yoke member 11 is an arcuate thumb engaging member 42, that is sized and configured for allowing the user to engage his thumb to the base member 24 of yoke 11, to move the yoke 11 in a sliding direction along the handle portion 30 of the first speculum member 12. A first receiving aperture 46 is generally rectangular and has rounded ends and is sized and configured for receiving the threaded rod 16 there through.

The upper end 26 of the yoke member 11 is generally "U" shaped, and includes first 48 and second 50 arms. The first and second arms 48, 50 each include an outwardly extending stud member 52 that provides a pivot pin for receiving the second speculum member 14. The yoke 11 is not generally linear but the handle portion 24 is angled relative to the yoke portion 26, at an angle about 10 to 20 degrees. The proximally facing surface of the base wall 32 of the yoke includes a series of ridges 57 or other surface features whose purpose is to increase the frictional resistance between the elevation nut 18 and the yoke 11 when the nut 18 is tightened to thereby resist relative movement between the nut 18 and the yoke 11 base wall 33.

The first speculum member 12 is best shown in FIGS. 2-5, 6, 8 and 13. The first speculum member 12 includes a generally rectangularly U-shaped portion that has a base 56 and a pair of side members 58 that are disposed in a plane generally perpendicular to the main plane of the base 56 of the handle portion 30. The base 56 and pair of side members 58 define a yoke receiving channel for slidably receiving the yoke member 11 within the yoke receiving channel.

The front surface 60 of the first handle member 30 includes surface features, such as a plurality of upraised pimples that help the user to stationarily position his hand on the front surface 60 of the handle member 30 by reducing the likelihood that his hand will slide on the surface. A foot portion 62 extends distally at the bottom of the handle member portion 30.

The proximal surface of the first handle portion 30 is sized and configured for slidably engaging the slidable base portion 24 of the yoke member 11, so that the yoke member 11 may slide along the handle portion 30 of the first speculum member 12.

A lower (or first) blade portion 32 is disposed at the top of the first handle portion or member 30. The lower blade portion 32 extends distally outwardly. In lateral cross-section, the lower blade portion 32 is generally arcuate. Generally, the overall exterior shape of the lower blade member 32 is similar to the blade found in many prior art speculums. The yoke member 11 is slidably receivable along a rearward portion of the first handle member 30 (or portion) of the first speculum member 12. The yoke member 11 is pivotably coupled with the second blade member 84 such that the second blade member 84 can pivot outwardly relative to the first blade member 32. The yoke member 11 is also configured to adjust an elevation between the first blade member 32 and the second blade member 84.

The blade portions 32, 18 of the first 12 and second 14 speculum members each include a proximal end 66 and a meatus engaging distal end 68. The proximal end 66 of the lower blade member 32 is generally open, with there being no proximal upstanding wall. The open proximal end 66 enables the user to sight along the interior 72 of the lower blade member 32 as defined by the upper surface 72 of the first, lower blade member 32.

The proximal end 66 of the lower blade portion 32 defines a portion of the aperture through which the user views the cavity into which the blade 32 is inserted. By virtue of its arcuate cross section, the upper surface 72 of the first blade 32 has a first side wall portion and a second side wall portion that is disposed generally parallel with and proximate to the first aide wall portion.

The first and second side wall portions define an interior channel therebetween that extends generally along the entire length of the first blade member 32 until it terminates at the "chin" portion of the distal end 68 of the blade 32. The second blade has a similar configuration, but is generally a mirror image of the first blade.

The first handle member 30 that is affixed to the blade 32 comprises generally a "trough" shaped channel, having a planar central portion 61, with two upstanding legs 58 disposed on either side of the central portion 61. The upstanding legs 58 of the first speculum member 12 are sized and configured for interiorly receiving the outwardly extending legs 36 of the yoke member 11.

An aperture 76 is formed in the handle portion 30 that preferably comprises a generally circular aperture 76, having side "flats". The side flats are sized and configured for receiving the head 78 of the threaded rod 16. The threaded rod 16 includes a head 78 that is generally circular in cross-section with flats, and is slightly smaller than the aperture 76 of the handle portion 30, so that the head 78 can be interiorly received within the circular flat shaped aperture of the first handle portion (or member) 30.

The flats prevent the head 78 of the threaded rod 16 from rotating in the aperture 76. Therefore, the rotational position of the threaded rod 16 is fixed. This fixed rotational position of the threaded rod 16 is useful, as it prevents the various elevation control nut 18 and spread control nut 20 from rotating the threaded rod 16 as the elevation control nut 18 and spread control nut 20 are rotated along the threads of the threaded rod 11.

The distal end 68 of the blade portion 32 is generally "chin" shaped so that it rises up accurately to enable the distal end 68 of the bottom surface of the blade 32, to meet the top surface lip 80. The upper surface of the blade 32 includes an upper lip 80 that is configured for being able to engage the corresponding lower lip 82 on the upper blade portion 86 of the second speculum member 16.

Figure 8:
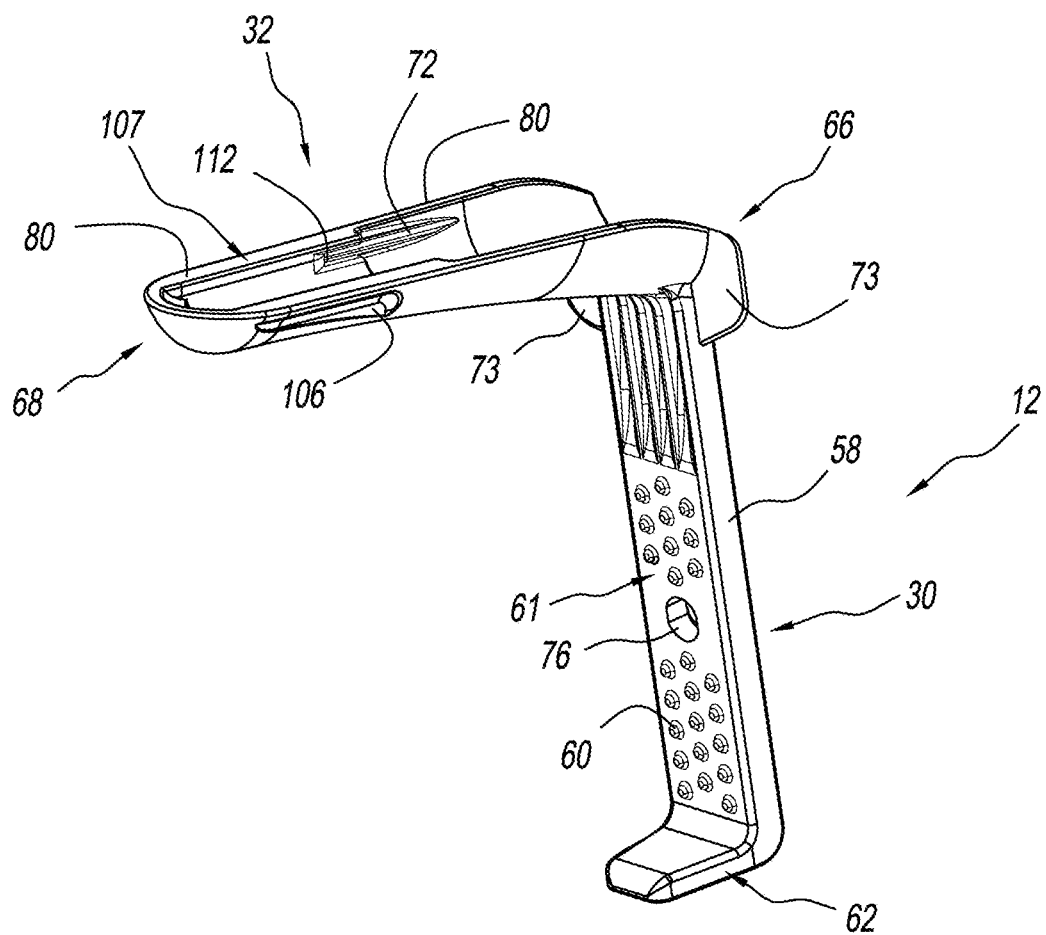
FIG. 8 is a perspective view of the first, or lower speculum member of the present invention that includes the lower blades.
Figure 9:
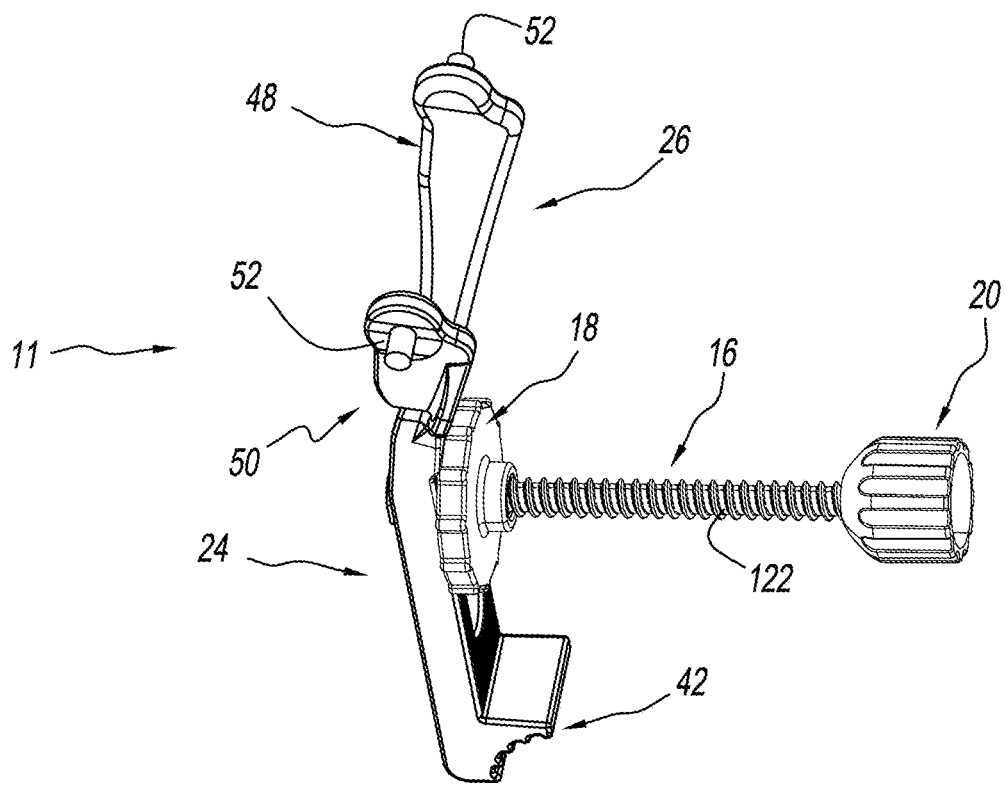
FIG. 9 is a perspective view of the yoke, threaded rod and first and second nut members of the present invention.
Figure 9A:
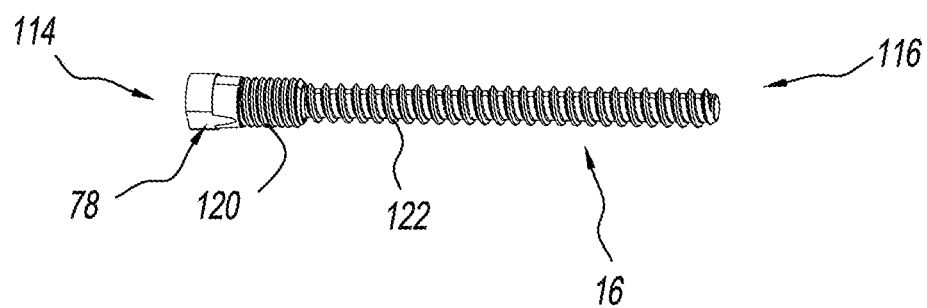
FIG. 9A comprises a perspective side view of the threaded rod.
Figure 12:
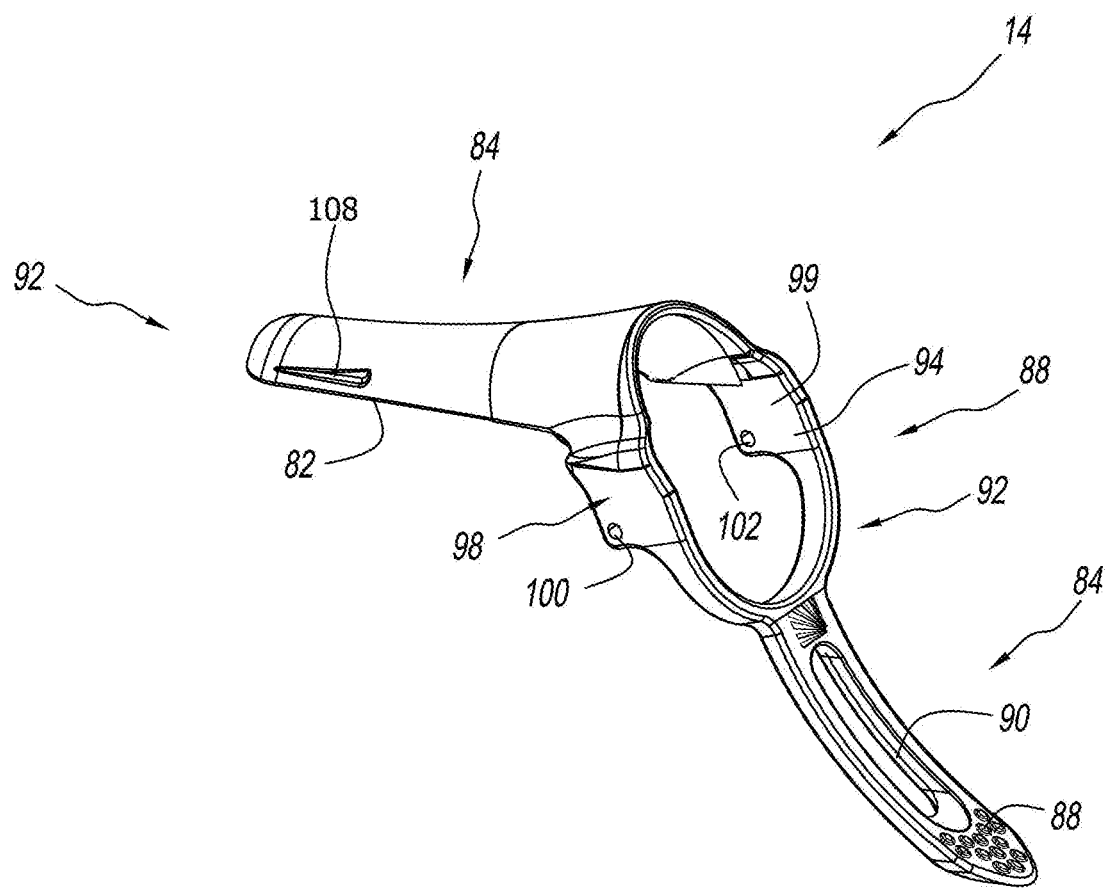
FIG. 12 is a perspective view of the second speculum member including the handle portion, aperture at the proximal end and upper blade member.
Figure 13:
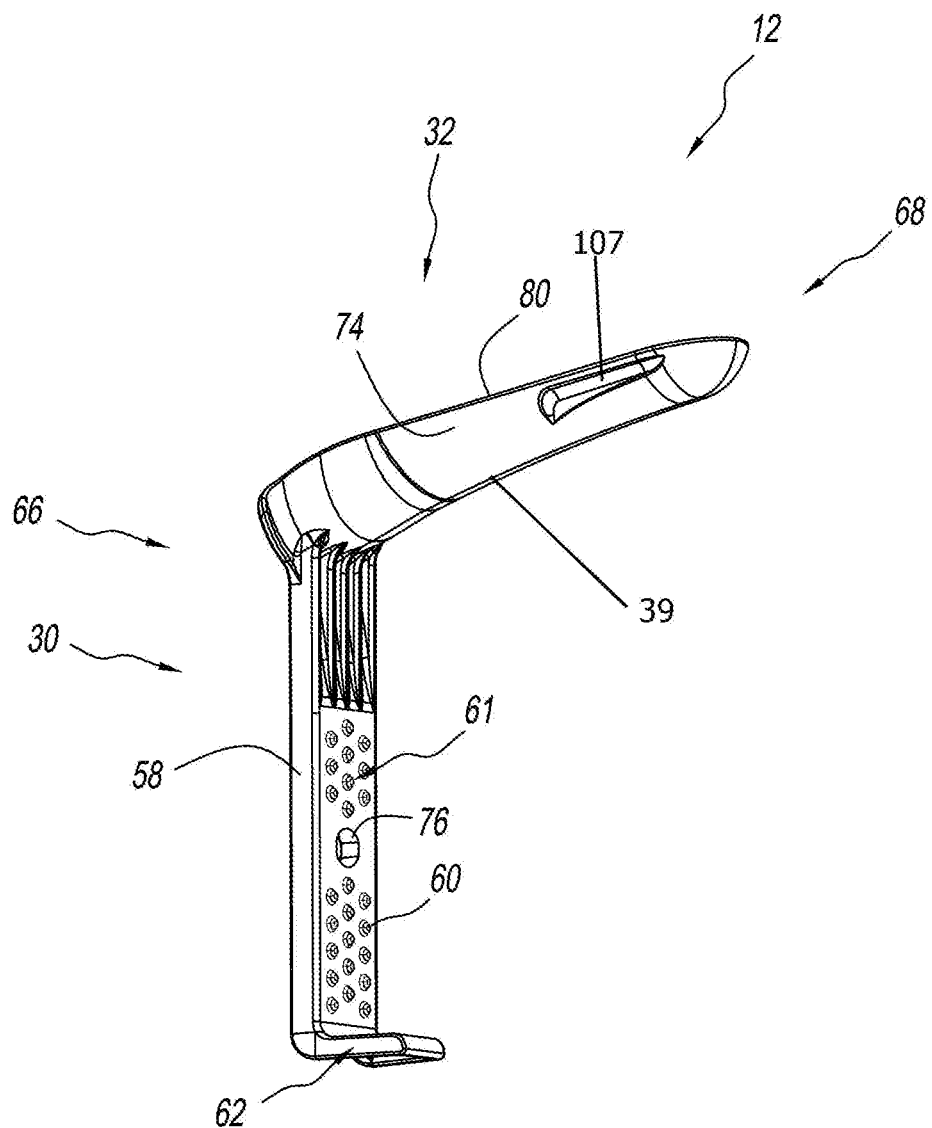
FIG. 13 is a perspective view of the first or lower speculum member that includes the first handle portion and the lower blade.
Figure 14:
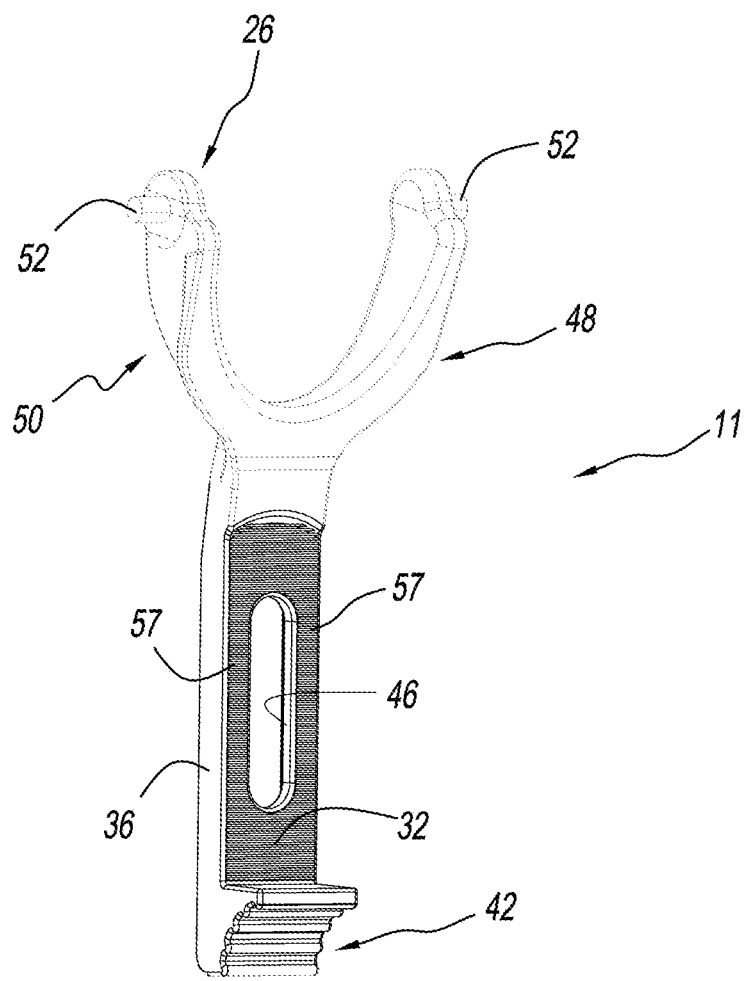
FIG. 14 is a proximal end biased perspective view of the yoke member including the handle engaging slider portion and the yoke portions.
Figure 15:
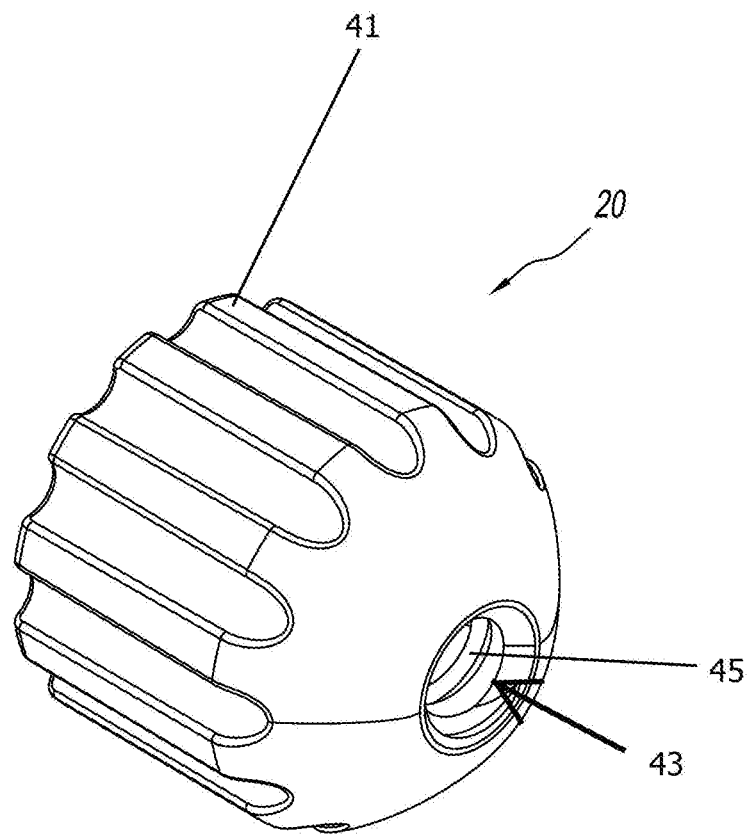
FIG. 15 is a perspective view of the second or spread nut member that is used to engage the first and second speculum member to fix the spread positions of the blades.
Figure 16:
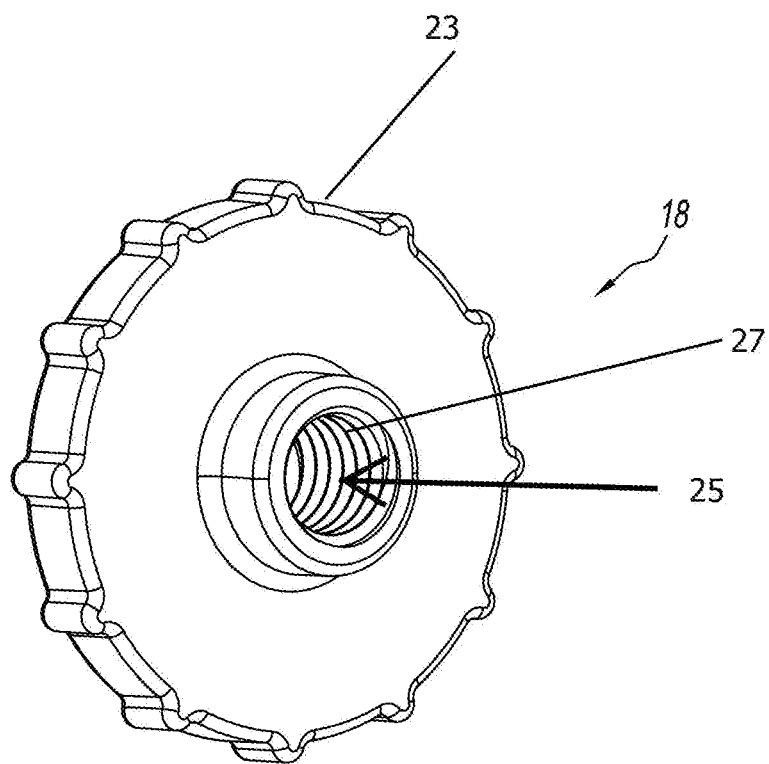
FIG. 16 is a perspective view of the elevation nut of the present invention that controls the elevation of the upper and lower blades with respect to each other.
Figure 17:
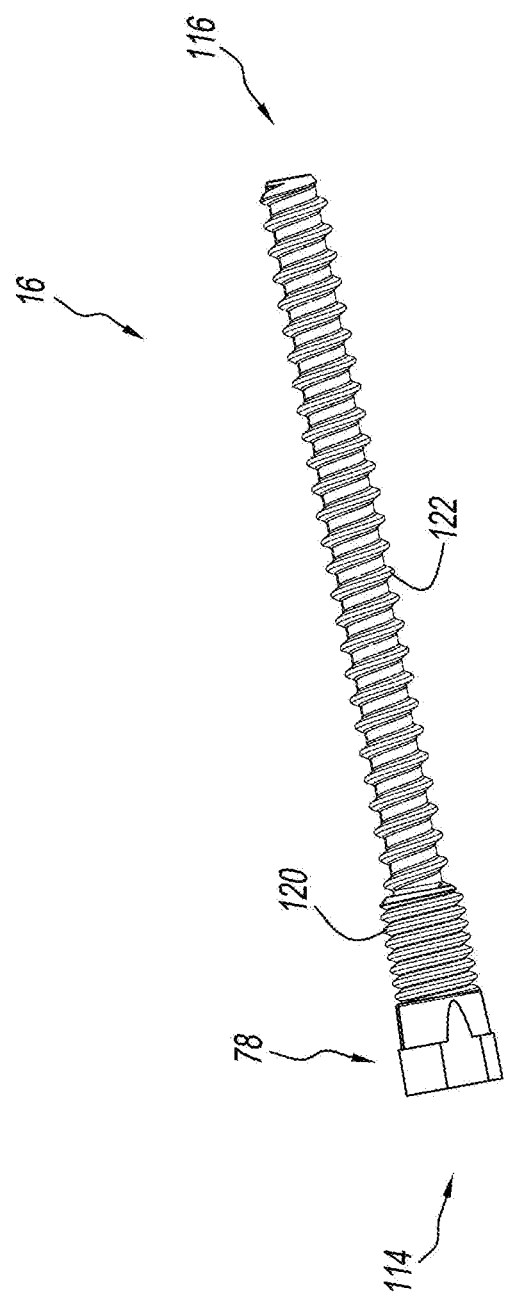
FIG. 17 is a side perspective view of the threaded rod of the present invention, noting that the threaded rod includes a head end that engages into the first handle, and a distal end that has an enlarged threaded portion to help keep the nut from being disengaged from the threaded rod.
Figure 18:
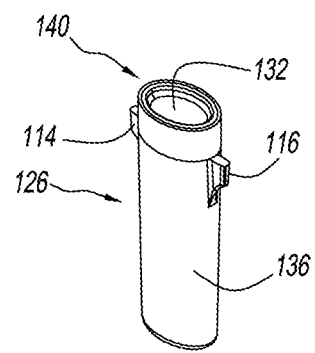
FIG. 18 is a front biased, perspective view of the luminescent chemical containing light cartridge of the present invention, with the top removed.
Figure 21:
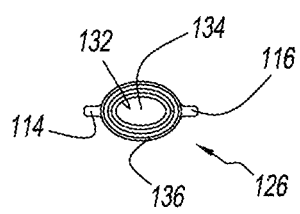
FIG. 21 is a top view of the light cartridge of the present invention.
Figure 19:
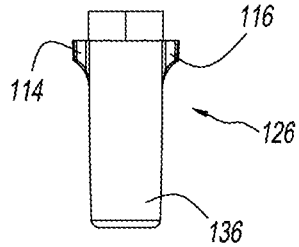
FIG. 19 is a front plan view of the light cartridge.
Figure 20:
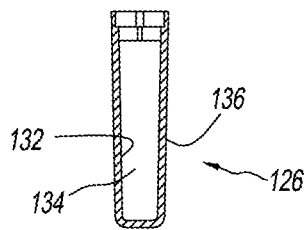
FIG. 20 is a sectional view taken along lines A-A of FIG. 19.
Figure 24:
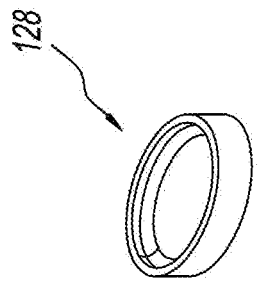
FIG. 24 is a perspective view of the light cartridge cap.
Figure 23:
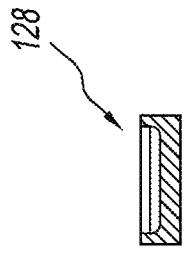
FIG. 23 is a sectional view taken along lines A-A of FIG. 22.
Figure 22:
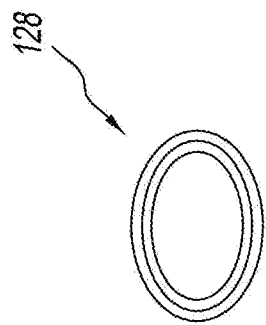
FIG. 22 is a top view of the cap member for enclosing the open top end of the light cartridge of FIG. 18.
Figure 25:
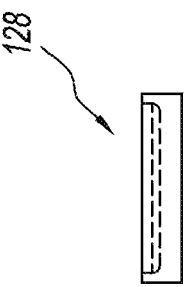
FIG. 25 is a side view of the cap of the light cartridge.

As is illustrated in FIG. 8, the first speculum member 12 can include anti-pinch tabs 73. The anti-pinch tabs 73 aid in preventing the tissue or pubic hair (not shown) of a patient from entering, and being pinched between the proximal portion 66 of the first blade portion 32 and the proximal end 90 of the second blade portion 84. Preventing such pinching of tissue or pulling of pubic hair by the anti-pinch tabs 73 can greatly reduce patient discomfort during an examination which is important to both patients and practitioners alike. Although it might seem minor, the Applicant has found that such pinching episodes are a major concern to practitioners, and their avoidance provides a significant advantage to the present invention.

The anti-pinch tabs 73 can extend outwardly from the upstanding legs 58 of the handle portion 30. The anti-pinch tabs 73 are depicted as connecting to the first blade portion 32, and are further depicted as extending outwardly further than the width of the first blade portion 32. The anti-pinch tabs 73 can include an outward curvature.

The upper or second speculum member 14 is best shown in FIGS. 3, 4, 5 and 12. The upper or second speculum member 14 has a lower, arcuate (or second) handle portion 86, a generally ring-shaped central portion 88 and a blade portion or member 84. The blade portion 84 includes a proximal end 66 and a distal end 68 that extends generally perpendicular to the handle portion 86. The handle portion 86 is generally arcuate, and may include one or more textured surfaces 88, to better help the user engage and direct the handle portion 86 without slipping.

A central, generally rounded end rectangular (paperclip shaped) second aperture 90 extends in the second handle portion 86, and provides a passageway through which the threaded rod 16 can pass.

The upper end of the handle portion 86 terminates in a generally ring-like sight aperture portion 92. The ring like portion includes a central sight aperture 94, that comprises the aperture of the speculum 10. In use, the user places his eye adjacent to the sight aperture 94 and looks down the blades 32, 84 into the cavity such as the vagina in which the blades 32, 84 are inserted.

The ring-like central portion 92 includes a pair of coupler portions 98, 99 that include a pair of laterally extending apertures 100, 102, with one aperture being formed in each of the two coupler portions 98, 99. The apertures 100, 102 are sized, positioned and configured for receiving the radially outwardly extending studs 50 of the yoke member 11, so that the upper blade 84 and handle 86 of the second speculum member 14 can be pivotably coupled to the yoke member 11.

The blade portion 84 comprises a shaped blade that is generally arcuate in lateral cross section to have a generally concave inner surface and a convex out surface. The blade 84 includes a lower lip member 82 that is sized and positioned to be placed in an opposed relationship with the upper lip member 80 of the lower blade. Generally, the width and length of the upper 84 and lower 32 blades are generally similar, except that the lower blade 32, is slightly longer than the upper blade 84, to give the speculum 10 something of an "under bite" configuration.

Each of the upper 32 and lower 84 blades includes a light cartridge engaging members 106, 107, 108, and 109, respectively. The light cartridge engaging members 106, 107, and 108 extend generally longitudinally along the side walls of the interior surface of upper 32 and lower 84 blades. The proximal end of the light cartridge engaging members 106, 107, 108, and 109 have a generally longitudinally extending receiving groove 112. The longitudinally extending groove 112 is sized and positioned for receiving a pair of opposed wing members 114, 116 that are formed on, and extend outwardly from the light cartridge.

The threaded rod 16, elevation control nut 18 and spread control nut 20 are best shown in FIGS. 1, 9, 9A, 16 and 17. The threaded rod 16 includes a handle engaging end 114 and a nut engaging end 116. The handle engaging end 114 includes a head 78. As discussed earlier, head 78 includes a flat containing circular cross section and is sized and configured for being inserted into the flat containing head receiving aperture 76 of the handle portion 30 of the first speculum member 12.

The threaded rod 16 also includes a first set of relatively fine threads 120 and a second set of relatively coarse threads 122. The fine threads 120 are placed and configured for receiving the threaded interior surface threads of the elevation control nut 18. The elevation control nut 18 is disposed between the slidable base 24 of the yoke 11, and the handle portion 86 of the second speculum blade 14. As discussed above, the handle portion 30 of the first speculum member 12 and the base member 24 of the yoke member 11 are slidably and fixedly positionable with respect to each other, to permit the user to adjust the engagement distance between the first 32 and second 84 blades.

The elevation control nut 18 is tightened against the base member 24 to urge the base member 24 into a frictional engagement with the handle portion 32 of the first speculum 12, so that the slidable movement between the yoke 11 and speculum member 12 is arrested, so thereby fixing the elevation between the first and second blade members 32, 84. When the user desires to change the elevation, one can loosen the elevation control nut 18, so that the handle portion 32 of the first speculum member 12 and yoke member 11 can move with respect to each other to change the engagement distance between the first and second blades 32, 84.

The spreading control nut member 20 has relatively more coarse threads 122, and is disposed exteriorly of the handle portion 86 of the second speculum member 14 that includes the upper blade 84. When the user desires to spread the speculum blades 32, 84 apart from each other, the user squeezes together the handle portions 30, 86 of the first and second speculum members 12, 14.

The compressive pressure of the vaginal walls in which the blades 32, 84 are inserted will tend to push the blade members 32, 84 together when they are inserted into the vagina and spread apart. As such, no mechanism is necessary to keep the blade members 32, 84 from moving further apart from each other. However, a mechanism is necessary to prevent the upper 84 and lower 32 blade members from pivotably moving in a direction closer together.

This is the function performed by the spread control nut member 20. In use, the user squeezes the first and second handle portions 30, 86 together until the speculum blades 32, 84 have spread within the vagina to a desired separation distance. At that point, the nut 20 is engaged to maintain the blade members 32, 84 of the first and second speculum members 12, 14 at the desired distance from each other.

For short, routine examinations, this fixing of the position of the blade members 32, 84 may not be necessary. However, when a procedure is being performed that requires a significant time period, or otherwise requires the user to employ his hands for purposes other than squeezing the handles 32, 84 together, the ability to fix the spread and elevation positions of the first and second blade members 32, 84 become most helpful, if not necessary. It has been found that the use of a relatively coarse thread, and a "sloppy"

tolerance between the spread control nut and rod 16 enables the user to "spin" the nut on the receiving shaft, so that with even a minor spin the nut will be able to make at least about two or more complete rotations on the shaft 16. This "sloppy" tolerance can be achieved by having the internal threads of the control nut oversized relative external threads of the threaded shaft such that the control nut freely spins upon the threaded shaft. This "spin" feature greatly reduces the time required for the practitioner to fixedly position the spread angle of the blade members 32, 84. In one non-limiting form, the threaded shaft can include approximately 13 threads per inch, a major diameter of the external threads of the threaded shaft can approximate 0.2 inches, and a minor diameter of the internal threads of the control nut can approximate 0.16 inches. In this form, the engagement between the external threads of the threaded shaft and the internal threads of the control nut can approximate 0.02 inches.

The light cartridge 22 is best shown in FIGS. 1A-5B, and FIGS. 18-29. The light cartridge 22 includes a generally cylindrically elliptical configured container 126 and includes a black opaque cap member 128. The use of the opaque cap at the proximal facing surface has the advantage of enhancing the user's vision by reducing the amount of light from the light cartridge that is being shined directly into the user's eyes. The container member 126 includes an interior surface 132 that defines a generally hollow interior 134, and an exterior surface 136. The exterior surface 136 includes cartridge retention members, such as a pair of laterally extending first and second wing members 114, 116 that are disposed near the upper open end 140 of the container 126.

The interior 134 of the container 126 is provided for receiving a chemiluminescent material therein that produces an optimal distributive lighting for about 15 minutes without harsh illumination. The chemiluminescent material may be similar to the materials disclosed in Cranor, U.S. Pat. Nos. 6,126,871 and 9,090,821, the disclosures of which are fully incorporated herein by reference.

After the chemiluminescent material is placed within the cartridge, the cap 128 of the cartridge (FIGS. 22-25) is placed over the upper opening of the cartridge container 126 and the unit is sealed. To activate the lighting of the chemiluminescent material, the cartridge 22 is squeezed and snapped. When the chemiluminescent material containing cartridge 22 is "snapped" and the chemiluminescent material therein is activated, a light source is produced that generates no heat.

In order for the chemiluminescent material to shine and illuminate the adjacent area, the container 126 must be made of a transparent or translucent plastic material. However, the use of a translucent or transparent material creates a problem, because exposing the chemiluminescent material to sunlight will tend to degrade the material and potentially make it less functional. Therefore, the speculum 10 and cartridge 22 are packaged in a manner so that the light cartridge 22 is contained within an opaque portion of the package so that light cannot enter the package and degrade the material in the cartridge 22.

In this regard, the Applicant has found that a two-compartment package can be provided that serves this function well. The first portion of the package is sized to receive the speculum 10 itself. As the speculum 10 may be made at a place remote from the place at which chemiluminescent lighting cartridge 22 is made, the package can be formed so that the portion of the package that contains the speculum 10 is sealed at the speculum factory, to prevent the speculum 10 from contacting any germs or other (substances). The portion of the package in which the cartridge 22 is placed can be left open, so that a cartridge 22 can be inserted at the cartridge factory. After the cartridge 22 is inserted, the second pouch can then be sealed.

Upon use, the cartridge 22 is coupled to one or both of the blade members 32, 84. As is best shown in FIGS. 2A-5B, each of the upper 84 and lower 32 blades includes a receiving member, here shown as longitudinally extending, inwardly raised first and second ridge members 106, 107, and 108 on the lower blade 32 and first and second ridge members 107, 109, of the second blade 84. One ridge member 106, 108 is provided in each of the two blade members 84, 32 so that the user has the option of placing the cartridge 22 in either the upper 84 or lower 32 blade at his discretion. Additionally, if so desired, the user may employ a pair of cartridges 22, 22A (FIG. 4A) with one cartridge 22A being coupled to the upper blade 84 and the second cartridge 22 coupled to the lower blade 32.

The proximal end of each of the raised ridge members 106, 107, 108, and 109 includes a wing engaging slot 112 that is sized and configured for snugly receiving and frictionally engaging the wing members 114, 116 that extends outwardly from the exterior surface 136 of the cartridge container 126.

The wing engaging slot 112 is sized to have a width just slightly smaller than the thickness of the wings 114, 116, so that the slots 112 snugly receive and frictionally engage the wings 114, 116 to fixedly position the cartridge 22 in the slot 112, so that the cartridge 22 will not become disengaged easily from the slot 112.

Currently cartridge 22 (when activated) will generate about 15 minutes of light, which thereby provides an illumination interval that is a greater duration than the time necessary to perform most examinations and procedures. However, if additional time is necessary, the cartridge 22 can be removed and replaced with a second "fresh" cartridge.

While the invention has been described in connection with what is presently considered to be the most practical and preferred embodiment, it is to be understood that the invention is not to be limited to the disclosed embodiment (s), but on the contrary, is intended to cover various modifications and equivalent arrangements included within the spirit and scope of the appended claims, which scope is to be accorded the broadest interpretation so as to encompass all such modifications and equivalent structures as permitted under the law.

Further, it should be understood that while the use of the word preferable, preferably, or preferred in the description above indicates that feature so described may be more desirable, it nonetheless may not be necessary and any embodiment lacking the same may be contemplated as within the scope of the invention, that scope being defined by the claims that follow.

In reading the claims it is intended that when words such as "a," "an," "at least one" and "at least a portion" are used, there is no intention to limit the claim to only one item unless specifically stated to the contrary in the claim. Further, when the language "at least a portion" and/or "a portion" is used the item may include a portion and/or the entire item unless specifically stated to the contrary.

What is claimed is:

1. An illuminated speculum, comprising:
    a first blade member extending from a proximal portion to a distal portion, wherein the first blade member includes a first side wall portion and a second side wall portion substantially opposite the first side wall portion, an interior channel located between the first side wall portion and the second side wall portion, a first receiving groove located at an interior surface of the first side wall portion, and a second receiving groove located at an interior surface of the second side wall portion;

a second blade member pivotally coupled with the first blade member, wherein the second blade member comprises a pair of opposing receiving grooves located at an interior surface of the second blade member;

a chemiluminescent cartridge configured to be removably coupled with either the first blade member or the second blade member, the chemiluminescent cartridge including a first retention tab extending outwardly from a first surface of the chemiluminescent cartridge, and a second retention tab extending outwardly from a second surface of the chemiluminescent cartridge, wherein the second surface is substantially opposite the first surface;

wherein the first retention tab is configured to be received and retained by the first receiving groove or a first one of the opposing receiving grooves, and the second retention tab is configured to be received and retained by the second receiving groove or a second one of the opposing receiving grooves, to removably couple the chemiluminescent cartridge with the first blade member or the second blade member; and wherein the chemiluminescent cartridge extends across a width of the interior channel when the chemiluminescent cartridge is coupled with the first blade member.

2. The illuminated speculum of claim 1, wherein the chemiluminescent cartridge includes a substantially elliptical cross-sectional profile, and wherein the interior surface of the first side wall portion and the interior surface of the second sidewall portion are substantially arcuate.

3. The illuminated speculum of claim 2, wherein an outer surface of the chemiluminescent cartridge abuts the substantially arcuate interior surfaces of the first and second side wall portions when the chemiluminescent cartridge is coupled to the first blade member.

4. The illuminated speculum of claim 3, wherein the first receiving groove and the second receiving groove are integrally formed with the first blade member.

5. The illuminated speculum of claim 1, wherein the chemiluminescent cartridge is configured to be coupled with the first blade member near the distal end of the first blade member.

6. A speculum, comprising:

a first blade member pivotally coupled with a second blade member, the first blade member operably coupled to a first handle member, and the second blade member operably coupled to a second handle member;

a chemiluminescent cartridge configured to be removably coupled with either first and second receiving grooves at an interior surface of the first blade member or first and second receiving grooves at an interior surface of the second blade member;

a yoke member slidably receivable along a rearward portion of the first handle member, wherein the yoke member is pivotally coupled with the second blade member such that the second blade member can pivot outwardly relative to the first blade member, and wherein the yoke member is configured to adjust an elevation between the first blade member and the second blade member;

a threaded rod coupled to the first handle member and extending rearwardly through a first aperture in the yoke member and through a second aperture in the second handle member;

an elevation retention member threadingly engaged with the threaded rod, wherein the elevation retention member is structured to selectively restrict movement of the yoke member relative the first handle member; and a pivot control member threadingly engaged with the threaded rod, wherein the pivot control member is configured to selectively restrict pivotal movement between the first blade member and the second blade member.

7. The speculum of claim 6, wherein the elevation retention member is threadingly engaged with the threaded rod at a location between the yoke member and the second handle member, and wherein the elevation retention member is configured to exert a force against the yoke member, thereby retaining the yoke member against the first handle member.

8. The speculum of claim 7, wherein the pivot control member is threadingly engaged with the threaded rod outwardly from the second handle member, and wherein the pivot control member is configured to exert a force against the second handle member.

9. The speculum of claim 8, wherein a lower portion of the yoke member further includes a rearwardly extending elevation adjustment mechanism.

10. The speculum of claim 8, wherein the second handle member further includes an arcuate shape.

11. The speculum of claim 8, wherein the rearward portion of the first handle member further includes a yoke member receiving channel, and wherein the yoke member is slidably received within the yoke receiving channel.

12. A speculum, comprising:

a first blade member pivotally coupled to a second blade member, wherein each of the first and second blade members extend from a proximal end to a distal end;

a chemiluminescent cartridge including a first retention tab extending outwardly from a first surface of the chemiluminescent cartridge, and a second retention tab extending outwardly from an opposite second surface of the chemiluminescent cartridge, the first and second retention tabs configured to be removably coupled with either first and second receiving grooves at an interior surface of the first blade member or first and second receiving grooves at an interior surface of the second blade member; and a speculum control including an elevation retention member and a pivot control nut each threadingly engaged with a threaded shaft, wherein the control nut and the threaded shaft each comprise a polymer, wherein internal threads of the pivot control nut are oversized relative to external threads of the threaded shaft such that the pivot control nut freely spins upon the threaded shaft, and wherein the pivot control nut is configured to continue rotation on the threaded shaft after a rotational force has been removed from the pivot control nut for at least 720 degrees of rotation of the pivot control nut about the threaded shaft.

13. The speculum of claim 12, wherein the pivot control nut is configured for controlling the pivot of the first and second blade members with respect to each other.

14. The speculum of claim 13, wherein the threaded shaft comprises 13 threads per inch.

15. The speculum of claim 14, wherein a major diameter of the external threads of the threaded shaft is 0.2 inches.

16. The speculum of claim 15, wherein a minor diameter of the internal threads of the pivot control nut is 0.16 inches.

17. The speculum of claim 16, wherein an allowance between the external threads of the threaded shaft and the internal threads of the pivot control nut is 0.02 inches.

18. A speculum, comprising:
- a first blade member operably coupled with a first handle member;
- a second blade member operably coupled with a second handle member, wherein each of the first and second blade members include opposing distal and proximal ends, and wherein the second handle member is located rearward of the first handle member; and
- an anti-pinch tab extending outwardly from an upper portion of the first handle member, wherein the anti-pinch tab is integrally formed with the first handle member, wherein the anti-pinch tab further extends upwardly toward the first blade member, and wherein the anti-pinch tab is configured to prevent tissue from entering near the proximal end of the first blade member.

19. The speculum of claim 18, further comprising two anti-pinch tabs extending outwardly from opposing sides of the first handle member.

20. The speculum of claim 19, wherein an outer portion of the anti-pinch tabs includes a curvature.

21. The speculum of claim 18, wherein an angle defined between the first blade member and the first handle member comprises an obtuse angle.

22. The speculum of claim 18, further comprising a yoke member slidably receivable along a rearward portion of the first handle member, wherein the yoke member is pivotally coupled with the second blade member such that the second blade member can pivot outwardly relative to the first blade member, and wherein the yoke member is configured to adjust an elevation between the first blade member and the second blade member.

* * * * *